(12) United States Patent
Liu et al.

(10) Patent No.: US 11,095,834 B2
(45) Date of Patent: Aug. 17, 2021

(54) LIVING ORGANISM IMAGE MONITORING SYSTEM AND METHOD

(71) Applicant: Pioneer Materials Inc. Chengdu, Sichuan (CN)

(72) Inventors: Chien-Chun Liu, Sichuan (CN); Liu-Yuh Lin, Sichuan (CN); Liang-Chih Weng, Sichuan (CN); Tzu-Huan Cheng, Sichuan (CN); Chen-Hsin Wu, Sichuan (CN); Hao-Che Liu, Sichuan (CN); Chien-Yao Huang, Sichuan (CN); Leon A Chiu, Sichuan (CN); Sau-Mou Wu, Sichuan (CN); Ti-Hsien Tai, Sichuan (CN); Yu-Hsiang Pan, Sichuan (CN)

(73) Assignee: PIONEER MATERIALS INC. CHENGDU, Sichuan (CN)

( * ) Notice: Subject to any disclaimer, the term of this patent is extended or adjusted under 35 U.S.C. 154(b) by 74 days.

(21) Appl. No.: 16/181,453

(22) Filed: Nov. 6, 2018

(65) Prior Publication Data
US 2019/0199942 A1    Jun. 27, 2019

(30) Foreign Application Priority Data

Dec. 22, 2017    (CN) .......................... 201711404811.8

(51) Int. Cl.
*A61B 5/01* (2006.01)
*H04N 5/33* (2006.01)
(Continued)

(52) U.S. Cl.
CPC ............. *H04N 5/33* (2013.01); *A61B 5/0077* (2013.01); *A61B 5/1455* (2013.01); *A61B 5/489* (2013.01);
(Continued)

(58) Field of Classification Search
CPC ..... A61B 5/0077; A61B 5/489; A61B 5/0037; A61B 5/1455; A61B 90/361;
(Continued)

(56) References Cited

U.S. PATENT DOCUMENTS

| 5,317,689 A | * | 5/1994 | Nack ...................... G09B 9/301 345/505 |
| 6,144,366 A | * | 11/2000 | Numazaki ............... G06F 3/011 345/156 |

(Continued)

FOREIGN PATENT DOCUMENTS

| CN | 104168814 A | 11/2014 |
| JP | 6003396 B2 | 10/2016 |
| WO | 2013163443 A2 | 10/2013 |

OTHER PUBLICATIONS

Office Action from corresponding EP Application No. 18204099.8, dated Jun. 19, 2019.
(Continued)

*Primary Examiner* — Philip P. Dang
(74) *Attorney, Agent, or Firm* — Workman Nydegger

(57) ABSTRACT

A living organism image monitoring system is provided, relating to the technical field of medical equipment. The living organism image monitoring system comprises a display module, a processor and a CIGS chip, the CIGS chip, the processor and the display module being electrically connected, the CIGS chip being used for detecting a near infrared light signal of a living organism and generating a current signal after having detected the near infrared light signal, the processor being used for generating a first pulse signal according to the current signal, and the display module being used for displaying an image according to the first pulse signal. The living organism image monitoring system provided by the present disclosure has the advantages of being capable of synchronously transmitting the
(Continued)

images of a living organism to the display module for display and enabling the images to be clearer.

12 Claims, 3 Drawing Sheets

(51) Int. Cl.
*A61B 5/1455* (2006.01)
*A61B 5/00* (2006.01)
*A61M 5/42* (2006.01)
*H04N 7/18* (2006.01)
*A61B 90/00* (2016.01)

(52) U.S. Cl.
CPC ............ *A61M 5/427* (2013.01); *H04N 7/183* (2013.01); *A61B 5/0037* (2013.01); *A61B 90/36* (2016.02); *A61B 90/361* (2016.02); *A61B 2562/0233* (2013.01)

(58) Field of Classification Search
CPC ........... A61B 2562/0233; A61B 90/36; A61M 5/427; H04N 5/33; H04N 7/183; H04N 7/18; H04N 5/2253
See application file for complete search history.

(56) References Cited

U.S. PATENT DOCUMENTS

| | | | | |
|---|---|---|---|---|
| 6,424,343 B1* | 7/2002 | Deering | ............ | G06K 9/00597 345/419 |
| 7,164,117 B2* | 1/2007 | Breed | ............... | B60R 21/01516 250/208.1 |
| 7,276,749 B2* | 10/2007 | Martin | .............. | H01L 27/14632 257/292 |
| 7,436,038 B2* | 10/2008 | Engelmann | .......... | H04N 5/3651 257/444 |
| 7,474,308 B2* | 1/2009 | Deering | .................... | G06T 5/20 345/419 |
| 7,596,242 B2* | 9/2009 | Breed | ................ | G06K 9/00362 382/103 |
| 8,828,786 B2* | 9/2014 | Miyazaki | ............ | H01L 31/0336 438/95 |
| 8,922,486 B2* | 12/2014 | Harland | ................ | G06F 3/0304 345/158 |
| 9,082,673 B2* | 7/2015 | Yu | ............................ | H01L 27/14 |
| 9,130,113 B2* | 9/2015 | Chiu | .................. | H01L 31/1884 |
| 9,306,098 B2* | 4/2016 | Huang | ................ | H01L 31/1864 |
| 9,368,659 B2* | 6/2016 | Cheng | ................. | H01L 31/0749 |
| 9,462,207 B2* | 10/2016 | Raynor | ................ | H04N 5/3452 |
| 9,583,655 B2* | 2/2017 | Cheng | ................ | H01L 31/0749 |
| 9,653,628 B2* | 5/2017 | Huang | .............. | H01L 21/02614 |
| 9,689,912 B2* | 6/2017 | Tsai | .................... | G01R 31/2642 |
| 9,748,419 B2* | 8/2017 | Cheng | ............. | H01L 31/022425 |
| 9,892,689 B2* | 2/2018 | Kang | ................... | G09G 3/3406 |
| 9,947,807 B2* | 4/2018 | Cheng | ............... | H01L 31/02021 |
| 10,027,933 B2* | 7/2018 | Won | ......................... | H04N 9/67 |
| 10,043,282 B2* | 8/2018 | Smits | ........................ | G01P 3/36 |
| 10,084,990 B2* | 9/2018 | Smits | ..................... | H04N 7/157 |
| 10,257,429 B2 | 4/2019 | Seto | | |
| 10,274,588 B2* | 4/2019 | Smits | ..................... | G01S 17/10 |
| 10,297,707 B1* | 5/2019 | Globus | ............... | H01L 31/0324 |
| 10,480,730 B1* | 11/2019 | Taylor | ................ | F21V 31/00 |
| 10,523,033 B2* | 12/2019 | Leabman | ................ | H02J 5/005 |
| 10,535,250 B2* | 1/2020 | Nihey | .................... | G08B 17/00 |
| 10,622,498 B2* | 4/2020 | Wang | .................. | H01L 31/077 |
| 2004/0109059 A1* | 6/2004 | Kawakita | ................. | H04N 7/18 348/143 |
| 2006/0164291 A1* | 7/2006 | Gunnarsson | ....... | G06K 19/0723 342/51 |
| 2012/0086095 A1 | 4/2012 | Nishiyama et al. | | |
| 2014/0261657 A1* | 9/2014 | Cheng | ................... | H01L 31/046 136/256 |
| 2014/0364690 A1 | 12/2014 | Seto | | |
| 2015/0000723 A1* | 1/2015 | Cheng | ..................... | H02S 40/44 136/248 |
| 2015/0136215 A1* | 5/2015 | Tsai | .................... | H01L 31/0749 136/256 |
| 2015/0241506 A1* | 8/2015 | Cheng | ................ | G01R 31/2601 324/761.01 |
| 2015/0249171 A1* | 9/2015 | Huang | .............. | H01L 21/02614 438/95 |
| 2015/0263195 A1* | 9/2015 | Huang | .............. | H01L 31/0465 136/256 |
| 2015/0287843 A1* | 10/2015 | Cheng | ................ | H01L 31/0749 136/256 |
| 2015/0303326 A1* | 10/2015 | Cheng | ................ | H01L 31/0463 136/256 |
| 2016/0337444 A1* | 11/2016 | Cameron | ................ | A24F 40/65 |
| 2018/0017679 A1* | 1/2018 | Valouch | ................ | A63F 13/655 |
| 2018/0136319 A1* | 5/2018 | Send | ........................ | G01S 17/46 |
| 2018/0159469 A1* | 6/2018 | Trupke | .................... | H02S 50/15 |
| 2018/0241582 A1* | 8/2018 | Nishimura | ............ | H04L 12/282 |
| 2019/0068931 A1* | 2/2019 | McCoy | ................. | G01J 3/0297 |

OTHER PUBLICATIONS

Communication under Rule 71(3) EPC from corresponding EP Application No. 18204099.8, dated May 13, 2020.
Office Action from corresponding CN Application No. 2017114048118, dated Oct. 28, 2019.
Notification to Grant Patent for corresponding CN Application No. 2017114048118, dated May 28, 2020.

* cited by examiner

LIVING ORGANISM IMAGE MONITORING SYSTEM AND METHOD

CROSS-REFERENCE TO RELATED APPLICATIONS

The present disclosure claims the priority of the Chinese patent application No. CN2017114048118, filed with the Chinese Patent Office on Dec. 22, 2017, and entitled "Living Organism Image Monitoring System", which is incorporated herein by reference in its entirety.

TECHNICAL FIELD

The present disclosure relates to the technical field of medical equipment, and particularly to living organism image monitoring system and method.

BACKGROUND ART

At present, when a doctor or a nurse injects patients or puts them on a drip, the subcutaneous blood vessels of some patients may not be easy to find, and as a result, multiple trials of puncturing are required, which makes the patients feel bad.

Accordingly, there currently are charge coupled device (CCD) image sensors and complementary metal oxide semiconductor (CMOS) image sensors, which make it possible to monitor subcutaneous blood vessels, however, neither the CCD image sensors nor the CMOS image sensors will obtain clear and ideal images, moreover, the CCD or CMOS image sensors are relatively bulky and are very inconvenient to use.

In view of this, how to solve the above problems is a major concern of a person skilled in the art.

SUMMARY

The technical solution adopted by the present disclosure is as follows:

In a first aspect, the present disclosure provides a living organism image monitoring system, which comprises a display module, a processor and a copper indium gallium selenide (CIGS) chip, the CIGS chip, the processor and the display module being electrically connected, the CIGS chip being used for detecting a near infrared light signal of a living organism and generating a current signal after having detected the near infrared light signal, the processor being used for generating a first pulse signal according to the current signal, and the display module being used for displaying an image according to the first pulse signal;
the CIGS chip comprising a plurality of CIGS modules arranged according to a predetermined rule, each of the CIGS modules being provided with a first address, and the processor being electrically connected to each of the CIGS modules and generating the first pulse signal after having received the current signal that is transmitted by one or more of the CIGS modules and contains the first address;
the processor being used for acquiring the number of pixels of the display module and the number of CIGS modules included in the CIGS chip, and calculating a ratio of the number of pixels to the number of CIGS modules included in the CIGS chip to further consider the maximum on load current magnitude and the quantity relative to the CIGS modules of the CIGS chip. According to the ratio, the first pulse signal is converted to a second pulse signal, the number of pulses of which is the same as the number of pixels, and the display module being used for displaying an image according to the second pulse signal.

In a second aspect, the present disclosure further provides another living organism image monitoring system, which comprises a display module and a copper indium gallium selenium (CIGS) chip, both the CIGS chip and the display module being communicatively connected to a processor, the CIGS chip being used for detecting an near infrared light signal of a living organism and generating a current signal after having detected the near infrared light signal, the processor being used for generating a first pulse signal according to the current signal, and the display module being used for displaying an image according to the first pulse signal;
the CIGS chip comprising a plurality of CIGS modules arranged according to a predetermined rule, each of the CIGS modules being provided with a first address, and the processor being electrically connected to each of the CIGS modules and generating the first pulse signal after having received the current signal that is transmitted by one or more of the CIGS modules and contains the first address;
the processor being used for acquiring the number of pixels of the display module and the number of CIGS modules included in the CIGS chip, calculating a ratio of the number of pixels to the number of CIGS modules included in the CIGS chip, and converting, according to the ratio, the first pulse signal to a second pulse signal, the number of pulses of which is the same as the number of pixels, and the display module being used for displaying an image according to the second pulse signal.

In a third aspect, the present disclosure provides a living organism image monitoring method, applied to the living organism image monitoring system as described above, the method comprising:
a CIGS chip detecting a near infrared light signal of a living organism and generating a current signal after having detected the near infrared light signal;
a processor generating a first pulse signal according to the current signal;
a display module displaying an image according to the first pulse signal;
the step of a CIGS chip detecting a near infrared light signal of a living organism and generating a current signal after having detected the near infrared light signal comprising: each CIGS module in the CIGS chip detecting a near infrared light signal of a living organism, one or more CIGS modules generating a current signal containing a first address after having detected the near infrared light signal, wherein the CIGS chip comprises a plurality of CIGS modules arranged according to a predetermined rule, and each of the CIGS modules is provided with a first address;
the step of a processor generating a first pulse signal according to the current signal comprising: the processor generating the first pulse signal after having received the current signal that is transmitted by one or more of the CIGS modules and contains the first address, the processor acquiring the number of pixels of the display module and the number of CIGS modules included in the CIGS chip, and calculating a ratio of the number of pixels to the number of CIGS modules included in the CIGS chip, and converting, according to the ratio, the first pulse signal to a second pulse signal, the number of pulses of which is the same as the number of pixels;
the step of a display module displaying an image according to the first pulse signal comprising: the display module displaying an image according to the second pulse signal.

BRIEF DESCRIPTION OF DRAWINGS

In order to more clearly illustrate the technical solutions of the present disclosure, brief description is made below on the drawings required to be used in the embodiments. It should be understood that the following drawings only illustrate some of the embodiments of the present disclosure and therefore shall not be regarded as a limitation to the scope, and for a person of ordinary skills in the art, other related drawings may be obtained from these drawings without inventive effort.

Figure 1:
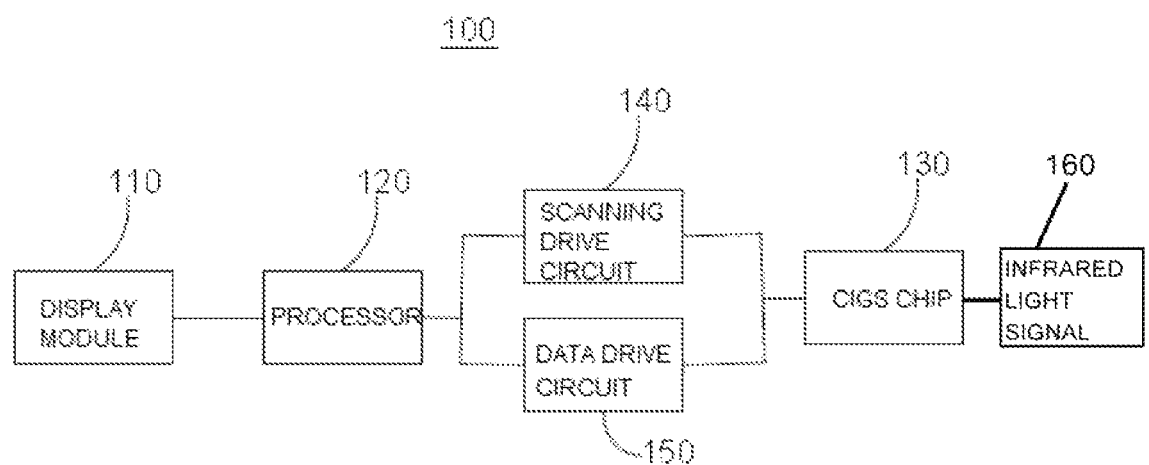
FIG. 1 is a schematic diagram of modules of a living organism image monitoring system provided by an embodiment of the present disclosure.

Reference signs: 100—living organism image monitoring system; 110—display module; 111—pixel group; 120—processor; 130—CIGS chip; 131—CIGS module; 1311—CIGS diode; 1312—MOS transistor; 140—scanning drive circuit; and 150—data drive circuit.

DETAILED DESCRIPTION OF EMBODIMENTS

In order to make the objects, technical solutions and advantages of the present disclosure clearer, the technical solutions of the present disclosure will be described clearly and completely below with reference to the drawings of the present disclosure. Apparently, the embodiments described are some of the embodiments of the present disclosure, rather than all of the embodiments. The components of the present disclosure described and illustrated in the drawings herein can generally be arranged and designed in a variety of different configurations.

The technical solutions of the present disclosure will be described clearly and completely below with reference to the drawings of the present disclosure. Apparently, the embodiments described are some of the embodiments of the present disclosure, rather than all of the embodiments. The components of the present disclosure described and illustrated in the drawings herein can generally be arranged and designed in a variety of different configurations. Thus, the following detailed description of the embodiments of the present disclosure provided in the drawings is not intended to limit the scope of the present disclosure claimed, but only represents the selected embodiments of the present disclosure. All the other embodiments that are obtained by a person skilled in the art on the basis of the embodiments of the present disclosure without inventive effort shall be covered by the protection scope of the present disclosure.

It should be noted that similar reference signs and letters denote similar items in the drawings, and therefore, once a certain item is defined in one figure, it does not need to be further defined or explained in the subsequent figures. Moreover, in the description of the present disclosure, it should further be noted that unless otherwise explicitly specified and defined, the terms "link" and "connect" shall be understood in broad sense, which may, for example, refer to fixed connection, detachable connection or integral connection; may refer to mechanical connection or electrical connection; and may also refer to direct connection, indirect connection by means of an intermediate medium, or communication between two elements. A person of ordinary skills in the art could understand the specific meaning of the terms in the present disclosure according to specific situations. Some embodiments of the present disclosure will be described in detail below with reference to the drawings. The following embodiments and the features of the embodiments can be combined with each other if there is no conflict.

In some embodiments, referring to FIG. 1, the present disclosure provides a living organism image monitoring system 100, which comprises a display module 110, a processor 120 and a CIGS (CuIn1-XGaXSe2 copper indium gallium selenide) chip, the CIGS chip 130, the processor 120 and the display module 110 being electrically connected.

In this embodiment, the CIGS chip 130 is used for detecting a near infrared light signal 160 of a living organism and generating a current signal after having detected the near infrared light signal. For example, the CIGS chip 130 may perform grid point image acquisition on an image of a real living object, and information of grid point image acquisition is a source of photosensitization of a micro-current signal array, i.e., a micro-current array generated by the living object due to the photosensitive mechanism. The processor 120 is used for generating a first pulse signal after having received the current signal (e.g., a micro-current array). The display module 110 is used for displaying an image according to the first pulse signal. When the hemoglobin concentration in the blood vessels of the living organism changes, the transmission and absorption of the near infrared rays will change regarding to the hemoglobin concentration, which makes it possible for the CIGS chip 130 to detect the near infrared light signal of the living object, so that the display module 110 can thereon display the image of the subcutaneous blood vessels of the living organism.

Compared with the CCD or CMOS image sensors, the CIGS chip 130 is smaller in volume, which thereby reduces the overall volume of the living organism image monitoring system 100. In order to further reduce the volume of the living organism image monitoring system 100, the display module 110, the processor 120 and the CIGS chip 130 can be integrally formed. That is, the living organism image monitoring system 100 has the functions of near infrared ray acquisition, signal processing and image display for the living organism, which thereby greatly reduces the volume.

Specifically, the CIGS chip 130 comprises a plurality of CIGS modules 131 arranged according to a predetermined rule, each CIGS module 131 is electrically connected to the processor 120, when one or more of the CIGS modules 131 has/have detected a near infrared light signal, e.g. subcutaneous blood vessels, a current signal will be generated, so that the processor 120 can generate a first pulse signal, e.g., a first voltage pulse signal, according to the current signal, so as to synchronously display the subcutaneous blood vessel of the living organism on the display module 110, thereby facilitating a doctor or a nurse inserting a needle into the blood vessel of a patient when injecting the patient or putting him on a drip.

In this embodiment, the display module 110 may be a micro-light emitting diode (Micro-LED) liquid crystal display screen, of course, in some other embodiments, the display module 110 may also be other devices, for example, a liquid crystal display (LCD), a plasma display, etc., which is not limited in this embodiment.

Figure 2:
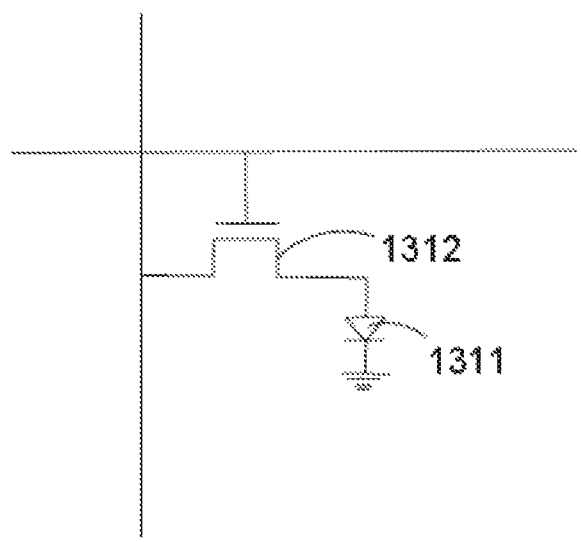
FIG. 2 is a schematic structural diagram of a CIGS module provided by an embodiment of the present disclosure.

Specifically, referring to FIG. 2, in this embodiment, each CIGS module 131 may comprise a MOS transistor 1312 and a CIGS diode 1311, the CIGS diode 1311 being electrically connected with the MOS transistor 1312, wherein the MOS transistor 1312 is a metal-oxide-semiconductor field effect transistor. When it is necessary to perform living organism image monitoring, a user may turn on the switch of the living organism image monitoring system 100, so that the power supply supplies power to the CIGS chip 130, so as to provide electrical energy to the MOS transistors 1312 of the CIGS modules 131 in the CIGS chip 130, after the MOS transistor 1312 is charged, as the gate of the MOS transistor 1312 is electrically conductive, thus the MOS transistor 1312 is turned on, when the CIGS diode 1311 has detected a near infrared light signal, e.g., a subcutaneous blood vessel, the CIGS diode 1311 is turned on so that the entire CIGS module 131 is turned on, thereby generating a current signal containing a first address. If there exists in the CIGS chip 130 one CIGS module 131 that is turned on, a current signal containing a first address corresponding to the turned-on CIGS module 131 will be generated, which signal is then subjected to a current-to-voltage conversion circuit and outputs as a voltage pulse that is transmitted to the processor 120. If there exist in the CIGS chip 130 two or more CIGS modules 131 that are turned on, each of the turned-on CIGS modules 131 will generate a current signal containing a first address corresponding to themselves, and transmit the current signal to the processor 120.

Meanwhile, in this embodiment, a plurality of CIGS modules 131 are arranged in a predetermined number of rows and a predetermined number of columns, so that a plurality of CIGS modules 131 are arranged in a rectangular shape. For example, the number of CIGS modules 131 is 400, then they are arranged in a manner of 20×20, of course, in some other embodiments, the CIGS modules 131 may also be arranged in other ways, which is not limited in this embodiment.

Furthermore, since each CIGS module 131 in the present embodiment comprises a MOS transistor 1312 and the turned-on state of the CIGS diode 1311 is controlled by the source (source selection button) of the MOS transistor 1312, each CIGS module 131 thus has a first address. The processor 120 acquires the micro-current signal array of the CIGS chip 130, that is, acquires the current signal which is transmitted by the CIGS chip 130 and carries the first address, and controls, according to the current signal, the display module 110 to display an image. In this embodiment, the processor 120 can convert the current signal carrying the first address to a first voltage pulse signal, and the processor 120 controls, according to the first voltage pulse signal, the display module 110 to display an image.

Figure 3:
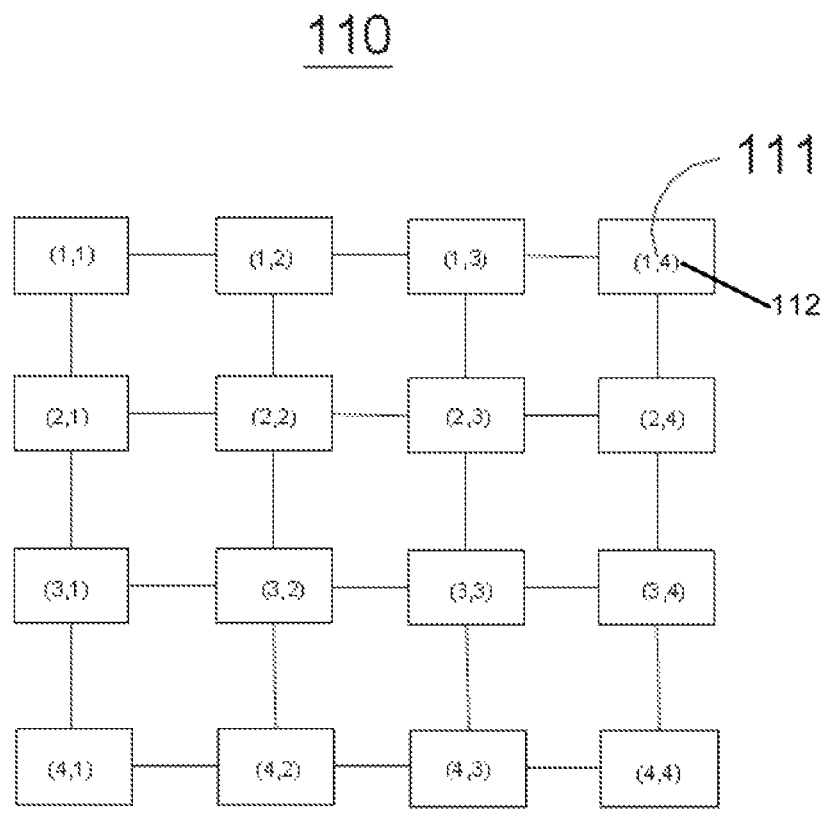
FIG. 3 is a partial schematic structural diagram of a display module provided by an embodiment of the present disclosure.

As an implementation of the present embodiment, referring to FIG. 3, the display module 110 comprises a plurality of pixel groups 111, each pixel group 111 comprises one or more pixels, each CIGS module 131 corresponds to one pixel group 111, and when any one of the CIGS modules 131 has detected an infrared light signal, the processor 120 will control the pixel group 111 corresponding to the CIGS module 131 to be lit. Accordingly, if two or more CIGS modules 131 have detected an infrared light signal, the processor 120 will control the pixel groups 111 corresponding to the two or more CIGS modules 131 to be lit simultaneously.

Moreover, a plurality of pixel groups 111 are arranged in a predetermined number of rows and a predetermined number of columns, and each pixel group 111 corresponds to a third address. The processor 120 stores a correlation between the third addresses and the first addresses, and the processor 120 is used for controlling, when any one of the CIGS modules 131 has detected an infrared light signal, the pixel group 111 whose third address corresponds to the first address of the CIGS module 131 to be lit. For example, when the display module 110 has 400 pixels and each pixel group 111 includes one pixel, i.e. each CIGS module 131 corresponds to one pixel group 111 and each pixel group 111 corresponds to a third address 112. For example, the third address of the pixel group 111 of the first row and the first column is (1, 1), the third address of the pixel group 111 of the first row and the second column is (1, 2), and when a certain CIGS module 131 has detected a subcutaneous blood vessel, the processor 120 can control, by means of addressing, the pixel group 111 whose third address corresponds to the first address of the CIGS module 131 to be lit. For example, if the correlation stored in the processor 120 includes that the CIGS module 131 whose first address is the first row and the first column corresponds to the pixel group 111 whose third address is (1, 1), then, when the CIGS module 131 of the first row and the first column has detected a subcutaneous blood vessel, the processor 120 can control the pixel group 111 whose third address is (1, 1) to be lit, i.e., control the one pixel included in the pixel group 111 to be lit.

Of course, in some other embodiments, each pixel group 111 may include more pixels, for example, when the display module 110 includes a total of 1600 pixels, each pixel group 111 includes four pixels, and the pixel groups 111 are still arranged in a manner of 20×20, if a certain CIGS module 131 has detected a subcutaneous blood vessel, the processor 120 can control, by means of addressing, the pixel group 111 corresponding to the CIGS module 131 to be lit, i.e., control the four pixels corresponding to the CIGS module 131 to be lit simultaneously. For example, if the pixel group 111 corresponding to the CIGS module 131 of the first row and the first column includes four pixels whose third addresses are (1, 1), (1, 2), (2, 1) and (2, 2), when the CIGS module 131 of the first row and the first column has detected a subcutaneous blood vessel, the processor 120 can control the pixel group 111 composed of four pixels whose third addresses are (1, 1), (1, 2), (2, 1) and (2, 2) to be lit.

Specifically, in this embodiment, in order to realize the function of site selection, the living organism image monitoring system 100 may further comprise a data drive circuit 150 and a scanning drive circuit 140, the processor 120, the scanning drive circuit 140, the data drive circuit 150 and the display module 110 being electrically connected. After having detected a current signal of the CIGS module 131, the processor 120 will convert, according to the current signal, the current signal of the first address to a corresponding first voltage pulse signal through a current-to-voltage conversion circuit, and the data drive circuit 150 and the scanning drive circuit 140 control, by processing the first voltage pulse signal, the corresponding pixel group 111 to be lit.

Specifically, in this embodiment, the first voltage pulse signal includes a set signal, a switching signal, a data signal, a first clock signal and a second clock signal. In the above the set signal (SETB) is a signal indicative of startup of the living organism image monitoring system 100, that is, when the living organism image monitoring system 100 is in an operation state, the set signal is always at a high level. The first clock signal (CLK1) is indicative of the state of all the rows of the arranged CIGS modules 131, the second clock signal (CLK2) is indicative of the state of each row of the arranged CIGS modules 131, the switching signal (CTRL) is a signal indicative of proceeding to scanning of a next frame picture after the scanning of all the CIGS modules 131 has been finished, and the data signal (DATA) is a signal of detection of a near infrared light signal, e.g., a signal of a subcutaneous blood vessel.

Description will be made below by way of example, in this embodiment, description is made using the CIGS modules 131 arranged in a manner of 20×20. Since there are 400 CIGS modules 131 in total, in the picture of each frame, the first clock signal has a total of 400 pulses. They are divided into 20 groups, the second pulse clock signal comprises 20 pulses, each pulse representing one row. In this case, when 20 pulses occur in the first clock signal, one pulse occurs in the second clock signal, indicating that the scanning of the first row has been finished and the process proceeds to the scanning of the next row, when 20 pulses occur in the first clock signal again, one pulse signal occurs in the second clock signal again, and so on. After the scanning of the 400 CIGS modules 131 has been finished, the process will proceed to the next scanning, i.e., the steps described above are repeated, and one frame of picture is formed after each scanning of the 400 CIGS modules 131, the display module 110 displays each frame of picture, thereby forming the images of a living organism. Moreover, when a certain CIGS module 131 has detected a subcutaneous blood vessel, one pulse will appear in the data signal, thereby controlling the corresponding pixel group 111 to be lit.

After scanning all the CIGS modules 131, the processor 120 generates a corresponding second pulse signal, and the data drive circuit 150 and the scanning drive circuit 140 can process the first pulse signal, thereby controlling the pixel group 111 on the display module 110 that corresponds to the third address to be lit.

On the one hand, the scanning drive circuit 140 can scan a rising edge of the first clock signal, of the second clock signal and of the data signal, and determine, according to the scanned rising edge, the third address of the pixel group 111 that needs to be lit. The data drive circuit 150 controls, according to the third address, the pixel group 111 corresponding to the third address to be lit.

The first address signal is a current signal of the CIGS module 131 that has been detected, and according to the current signal, the current signal of the first address is converted to a corresponding first voltage pulse signal through a current-to-voltage conversion circuit. The second address signal is a second address scan pulse generated before switching to the next column after the data pulse of each displayed column has been scanned. The third address signal is a third address scan pulse generated before switching to the next picture after the data pulse of each displayed picture has been scanned.

On the other hand, the scanning drive circuit 140 can scan a falling edge of the first clock signal, of the second clock signal and of the data signal, and determine, according to the fallen scanning, the third address of the pixel group 111 that needs to be lit. The data drive circuit 150 controls, according to the third address, the pixel group 111 corresponding to the third address to be lit, thereby achieving the effect of synchronously displaying the subcutaneous blood vessels of the living organism on the display module 110.

Optionally, in the present disclosure, the first address, the second address and the third address may be determined based on the rising edge and the falling edge in the following manner.

The principle of implementation of determining the first address based on the rising edge and the falling edge is as follows: after the currently displayed grid points have been scanned, calculation needs to be performed via a micro processing system and a first pulse signal (CLK1) is output, and the positions of the grid points where small current (which is converted to a voltage pulse through the current-to-voltage conversion circuit) is formed due to the irradiation of infrared light are scanned.

The principle of implementation of determining the second address based on the rising edge and the falling edge is as follows: for the currently displayed column, after all the grid points of the entire column have been displayed, calculation needs to be performed via a micro processing system and a second voltage pulse signal (CLK2) is output, the next column is directly displayed and updated, and this CLK2 does not need to be determined based on the rising edge and the falling edge.

The principle of implementation of determining the third address based on the rising edge and the falling edge is as follows: for the currently displayed picture, after all the grid points of the entire picture have been displayed, calculation needs to be performed via a micro processing system and a third pulse signal (CTRL) is output, the picture is directly displayed and updated, and this CTRL does not need to be determined based on the rising edge and the falling edge.

As another implementation of the present embodiment, the display module 110 comprises a plurality of pixels, each pixel being provided with a second address, with the development of science and technology, the pixel solution of the display module 110 will be higher and higher, that is, the display module 110 will comprise more and more pixels, in view of this, the inventor has developed another display mode.

In the present disclosure, the number of pixels and the number of CIGS modules may be flexibly set, in one example, the number of pixels may be larger than the number of CIGS modules, in another example, the number of pixels may be equal to the number of CIGS modules, and in a further example, the number of pixels may be smaller than the number of CIGS modules. The ratio of the number of pixels to the number of CIGS modules varies as the number of pixels and the number of CIGS modules vary.

Taking the case as an example where the number of pixels of the display module 110 is larger than the number of CIGS modules 131, in order to control the display module 110 to display an image by using a pulse signal, the processor 120 will process the pulse signal.

In this embodiment, in order to realize image display, the processor 120 will first acquire the number of pixels of the display module 110 and the number of CIGS modules 131, and then calculate the ratio of the number of pixels to the number of CIGS modules 131. Moreover, the processor 120 can acquire a micro current signal array of the CIGS chip 130, i.e., acquire the current signal of the CIGS chip 130 carrying the first address, thereby generating a first pulse signal. In the above, the number of pulses of the first pulse signal is different from the number of pixels of the display module 110. In order to enable the number of pulses of the pulse signal to be the same as the number of pixels, the processor 120 will process the first pulse signal.

Since the processor 120 has calculated the ratio of the number of pixels to the number of CIGS modules 131, the processor 120 will split the first pulse signal, so that each pulse signal is split into pulse signals the number of which is the same as the ratio, thereby being converted to a second pulse signal, the number of pulses in the second pulse signal is the same as the number of pixels of the display module 110.

Figure 4:
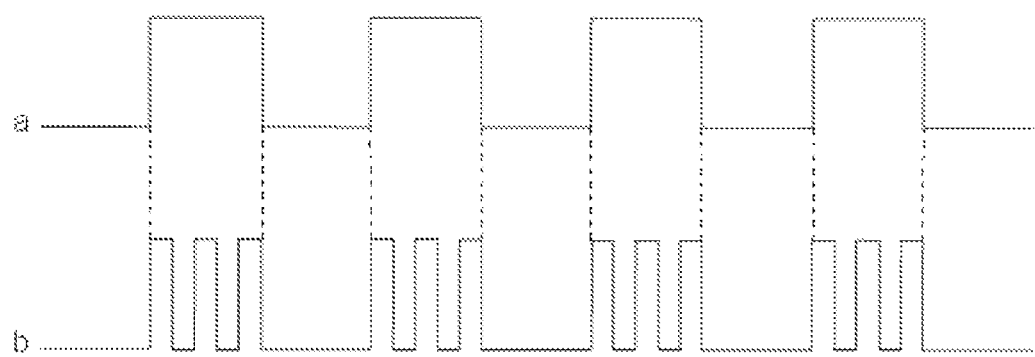
FIG. 4 is a pulse signal diagram provided by another embodiment of the present disclosure.

Description is made below by way of example, referring to FIG. 4, for example, the number of pixels is three times the number of CIGS modules 131, then after acquiring the first pulse signal (the pulse signal a in FIG. 4), the processor 120 will split each pulse into three pulses, in this way, the first pulse signal is converted to a second pulse signal (the pulse signal b in FIG. 4), and therefore through the second pulse signal, the display module 110 is controlled to display an image. Of course, in some other embodiments, the ratio of the number of pixels to the number of CIGS modules 131 may be greater, then the processor 120 needs to split each pulse in the first pulse signal into more pulses so as to obtain the second pulse signal.

Moreover, each pixel is provided with a second address, and the second pulse signal includes a set signal, a switching signal, a data signal, a first clock signal and a second clock signal, the display module 110 is used for lighting the pixels whose second addresses correspond to the set signal, the switching signal, the data signal, the first clock signal and the second clock signal. It should be noted that in the embodiment, FIG. 4 merely shows the pulse signal pattern of the first clock signal.

Furthermore, the living organism image monitoring system 100 further comprises a data drive circuit 150 and a scanning drive circuit 140, wherein the processor 120, the scanning drive circuit 140, the data drive circuit 150 and the display module 110 are electrically connected, the scanning drive circuit 140 is used for scanning the rising edge or the falling edge of the first clock signal, of the second clock signal and of the data signal, and the data drive circuit 150 is used for controlling, according to the rising edge or the falling edge of the first clock signal, of the second clock signal and of the data signal, the pixels whose second addresses match the first clock signal, the second clock signal and the data signal to be lit.

In order to further reduce the overall volume of the living organism image monitoring system 100, the display module 110, the processor 120 and the CIGS chip 130 may be integrally formed.

Figure 5:
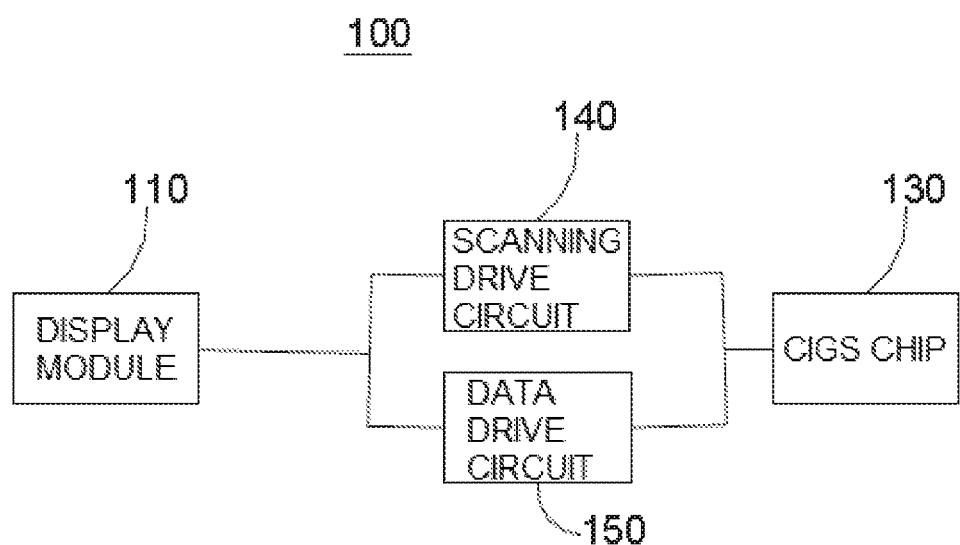
FIG. 5 is a schematic diagram of modules of a living organism image monitoring system provided by another embodiment of the present disclosure.

Optionally, in some embodiments, referring to FIG. 5, the present disclosure provides a living organism image monitoring system 100, the living organism image monitoring system 100 comprises a display module 110 and a CIGS (CuIn1-XGaXSe2 copper indium gallium selenide) chip, the CIGS chip 130 and the display module 110 being both communicatively connected to a processor 120. It should be noted that, since the living organism image monitoring system 100 provided in this embodiment and the living organism image monitoring system 100 provided in the first embodiment are largely the same in structure and function, in order to avoid redundant description, only the differences therebetween are described below, and as to the same parts therebetween, reference can be made to the first embodiment.

In this embodiment, in order to reduce the volume of the living organism image monitoring system 100, the display module 110 and the CIGS chip 130 are integrally formed, i.e., the living organism image monitoring system 100 has the functions of near infrared ray acquisition and image display for a living organism, thereby greatly reducing the volume. Moreover, in this embodiment, the processor 120 may be an intelligent terminal device such as a computer, and the display module 110 and the CIGS chip 130 may be communicatively connected with the processor 120 in a wired or wireless manner, thereby transmitting signals to the processor 120 for processing, and the processed signals are transmitted to the display module 110 for display.

In addition, the present disclosure further provides a living organism image monitoring method, which is applied to the living organism image monitoring system, the method comprising: a CIGS chip detecting a near infrared light signal of a living organism and generating a current signal after having detected the near infrared light signal; a processor generating a first pulse signal according to the current signal; and a display module displaying an image according to the first pulse signal.

In the above, the step of a CIGS chip detecting a near infrared light signal of a living organism and generating a current signal after having detected the near infrared light signal comprises: each CIGS module in the CIGS chip detecting a near infrared light signal of a living organism, one or more CIGS modules generating a current signal containing a first address after having detected the near infrared light signal, wherein the CIGS chip comprises a plurality of CIGS modules arranged according to a predetermined rule, and each of the CIGS modules is provided with a first address.

The step of a processor generating a first pulse signal according to the current signal comprises: the processor generating the first pulse signal after having received the current signal that is transmitted by one or more of the CIGS modules and contains the first address, the processor acquiring the number of pixels of the display module and the number of CIGS modules included in the CIGS chip, calculating a ratio of the number of pixels to the number of CIGS modules included in the CIGS chip, and converting, according to the ratio, the first pulse signal to a second pulse signal, the number of pulses of which is the same as the number of pixels.

The step of a display module displaying an image according to the first pulse signal comprises: the display module displaying an image according to the second pulse signal.

Optionally, each of the CIGS modules comprises a MOS transistor and a CIGS diode, the CIGS diode being electrically connected with the MOS transistor. The step of one or more CIGS modules generating a current signal containing a first address after having detected the near infrared light signal comprises: supplying power to the CIGS chip using a power supply, so that the MOS transistors of the CIGS modules in the CIGS chip are turned on; the CIGS diodes of the CIGS modules performing near infrared light signal detection after the MOS transistors of the CIGS modules are turned on and being turned on after a near infrared light signal has been detected, and generating a current signal containing a first address.

Optionally, the step of the display module displaying an image according to the second pulse signal comprises: the processor controlling the pixel groups corresponding to the CIGS modules that have detected an infrared light signal in the display module to be lit, wherein the display module comprises a plurality of pixel groups, each of the pixel groups includes one or more pixels, and each of the CIGS modules corresponds to one of the pixel groups.

Optionally, the step of the processor controlling the pixel groups corresponding to the CIGS modules that have detected an infrared light signal in the display module to be lit comprises: the processor controlling, when any one of the CIGS modules has detected an infrared light signal, the pixel group whose third address corresponds to the first address of the CIGS module to be lit, wherein the processor stores a correlation between the third addresses and the first addresses.

As to the implementation principle and the working flow of the method embodiment, reference can be made to the corresponding description in the above system embodiment, which will not be further described herein.

In summary, the present disclosure provides living organism image monitoring system and method, the living organism image monitoring system comprises a display module, a processor and a CIGS chip, wherein the CIGS chip, the processor and the display module are electrically connected, the CIGS chip is used for detecting a near infrared light signal of a living organism and generating a current signal after having detected a near infrared light signal, the processor is used for generating a first pulse signal after having received the current signal, and the display module is used for displaying an image according to the first pulse signal. In the above, the CIGS chip comprises a plurality of CIGS modules, the processor is used for converting, according to the ratio of the number of pixels to the number of CIGS modules, the first pulse signal to a second pulse signal of which the number of pulses is the same as the number of pixels, and the display module is used for displaying an image according to the second pulse signal. When the hemoglobin concentration in the blood vessels of a human body changes, the near infrared rays will transmit and absorb the change of the hemoglobin concentration, that is, when the hemoglobin concentration changes, the CIGS chip can detect the near infrared light signal of the living organism, i.e., can detect the subcutaneous blood vessels of the living organism, and also synchronously transmit the images of subcutaneous blood vessels to the display module for display, and the images are relatively clear. Moreover, since the CIGS chip in the living organism image monitoring system provided by the present disclosure is relatively small, the overall volume of the living organism image monitoring system is relatively small. By integrally forming the display module, the processor and the CIGS chip, it is possible to further reduce the volume.

It should be noted that, in the text, the relational terms such as "first" and "second" are only used to distinguish one entity or operation from another entity or operation, and do not necessarily require or imply that any such actual relationship or sequence exists between these entities or operations. Moreover, the term "comprising", "including", or any other variant thereof is intended to encompass a non-exclusive inclusion, so that the process, method, article or device comprising a series of elements not only comprises these elements, but also comprises other elements not explicitly listed, or further comprises inherent elements of the process, method, article or device. In cases where no further limitations are made, the element defined with the statement "including one . . . " does not exclude the case that other identical elements further exist in the process, method, article or device comprising the elements.

The descriptions above are only preferred embodiments of the present disclosure, which are not used to restrict the present disclosure. For those skilled in the art, the present disclosure may have various changes and variations. Any modifications, equivalent substitutions, improvements etc. within the spirit and principle of the present disclosure shall all be included in the scope of protection of the present disclosure. It should be noted that similar reference signs and letters denote similar items in the drawings, and therefore, once a certain item is defined in one figure, it does not need to be further defined or explained in the subsequent figures.

INDUSTRIAL APPLICABILITY

The living organism image monitoring system and method provided by the present disclosure are capable of detecting a near infrared light signal of a living organism and transmitting the images to a display module for display, and the images are relatively clear. The CIGS chip is relatively small, which thereby reduces the overall volume of the living organism image monitoring system.

The invention claimed is:

1. A living organism image monitoring system, wherein the living organism image monitoring system comprises a display module, a processor and a copper indium gallium selenide (CIGS) chip, the CIGS chip, the processor and the display module are electrically connected, the CIGS chip is used for detecting near infrared light of a living organism and generating a current after detecting the near infrared light of the living organism, the processor is used for generating a first pulse according to the current, and the display module is used for displaying an image according to the first pulse;

the CIGS chip comprises a plurality of CIGS modules arranged according to a predetermined rule, each of the plurality of CIGS modules is provided with a first address, and the processor is electrically connected to each of the plurality of CIGS modules and generates the first pulse after receiving the current that is transmitted by one or more of the plurality of CIGS modules and contains the first address;

the processor is used for acquiring a number of pixels of the display module and a number of CIGS modules included in the CIGS chip, calculating a ratio of the number of pixels of the display module to the number of CIGS modules included in the CIGS chip, and converting, according to the ratio, the first pulse to a second pulse, a number of pulses of the second pulse is equal to the number of pixels of the display module, and the display module is used for displaying an image according to the second pulse, wherein the display module comprises a plurality of pixel groups, each pixel group of the plurality of pixel groups comprises one or more pixels, each of the plurality of CIGS modules corresponds to one pixel group, and the processor is used for controlling a pixel group to be lit, when any one of the plurality of CIGS modules detects infrared light, wherein the controlled pixel group to be lit corresponding to the one of the plurality of CIGS modules, wherein the plurality of pixel groups are arranged in a predetermined number of rows and a predetermined number of columns, and each pixel group of the plurality of pixel groups corresponds to a third address, the processor stores a correlation between third addresses and first addresses, and the processor is used for controlling the pixel group to be lit, when any one of the plurality of CIGS modules detects the infrared light, wherein the controlled pixel group to be lit having the third address corresponding to the first address of the CIGS module, wherein the plurality of CIGS modules are arranged in a predetermined number of rows and a predetermined number of columns, so that the plurality of CIGS modules are arranged in a rectangular shape, wherein each pixel of the display module is provided with a second address, and the second pulse includes a set indicator, a switching indicator, a data indicator, a first clock indicator and a second clock indicator, the display module is used for lighting the pixels of the display module whose second addresses correspond to the data indicator, the first clock indicator and the second clock indicator;

wherein the set indicator is used to indicate a startup of the living organism image monitoring system;

the switching indicator is used to indicate a starting of scanning of a next frame picture after the scanning of all the CIGS modules is finished;

the data indicator is used to indicate a detection of the near infrared light of the living organism;

the first clock indicator is used to indicate a state of all the rows of the arranged CIGS modules; and the second clock indicator is used to indicate a state of each row of the arranged CIGS modules.

2. The living organism image monitoring system according to claim 1, wherein the living organism image monitoring system further comprises a data drive circuit and a scanning drive circuit, the processor, the scanning drive circuit, the data drive circuit and the display module are electrically connected, the scanning drive circuit is used for scanning a rising edge or a falling edge of the first clock indicator, of the second clock indicator and of the data indicator, and the data drive circuit is used for controlling pixels of the pixel group to be lit, according to the rising edge or the falling edge of the first clock indicator, of the second clock indicator and of the data indicator, wherein the controlled pixels of the pixel group to be lit having the second addresses matching the first clock indicator, the second clock indicator and the data indicator.

3. The living organism image monitoring system according to claim 1, wherein each of the plurality of CIGS modules comprises a MOS transistor and a CIGS diode, the CIGS diode is electrically connected with the MOS transistor, the MOS transistor is in a turned-on state when being charged, and the CIGS diode is used for being turned on to generate the current after detecting the near infrared light of the living organism.

4. The living organism image monitoring system according to claim 1, wherein the display module, the processor and the CIGS chip are integrally formed.

5. A living organism image monitoring system, wherein the living organism image monitoring system comprises a display module and a copper indium gallium selenium (CIGS) chip, both the CIGS chip and the display module are communicatively connected to a processor, the CIGS chip is used for detecting near infrared light of a living organism and generating a current after detecting the near infrared light of the living organism, the processor is used for generating a first pulse according to the current, and the display module is used for displaying an image according to the first pulse;

the CIGS chip comprises a plurality of CIGS modules arranged according to a predetermined rule, each of the plurality of CIGS modules is provided with a first address, and the processor is electrically connected to each of the plurality of CIGS modules and generates the first pulse after receiving the current that is transmitted by one or more of the plurality of CIGS modules and contains the first address;

the processor is used for acquiring a number of pixels of the display module and a number of CIGS modules included in the CIGS chip, calculating a ratio of the number of pixels of the display module to the number of CIGS modules included in the CIGS chip, and converting, according to the ratio, the first pulse to a second pulse, a number of pulses of the second pulse is equal to the number of pixels of the display module, and the display module is used for displaying an image according to the second pulse, wherein the display module comprises a plurality of pixel groups, each pixel group of the plurality of pixel groups comprises one or more pixels, each of the plurality of CIGS modules corresponds to one pixel group, and the processor is used for controlling a pixel group to be lit, when any one of the plurality of CIGS modules detects infrared light, wherein the controlled pixel group to be lit corresponding to the one of the plurality of CIGS modules, wherein the plurality of pixel groups are arranged in a predetermined number of rows and a predetermined number of columns, and each pixel group of the plurality of pixel groups corresponds to a third address, the processor stores a correlation between third addresses and first addresses, and the processor is used for controlling the pixel group to be lit, when any one of the plurality of CIGS modules detects the infrared light, wherein the controlled pixel group to be lit having the third address corresponding to the first address of the CIGS module, wherein the plurality of CIGS modules are arranged in a predetermined number of rows and a predetermined number of columns, so that the plurality of CIGS modules are arranged in a rectangular shape, wherein each pixel of the display module is provided with a second address, and the second pulse includes a set indicator, a switching indicator, a data indicator, a first clock indicator and a second clock indicator, the display module is used for lighting the pixels of the display module whose second addresses correspond to the data indicator, the first clock indicator and the second clock indicator;

wherein the set indicator is used to indicate a startup of the living organism image monitoring system; the switching indicator is used to indicate a starting of scanning of a next frame picture after the scanning of all the CIGS modules is finished; the data indicator is used to indicate a detection of the near infrared light of the living organism; the first clock indicator is used to indicate a state of all the rows of the arranged CIGS modules;

and the second clock indicator is used to indicate a state of each row of the arranged CIGS modules.

6. The living organism image monitoring system according to claim 5, wherein the living organism image monitoring system further comprises a data drive circuit and a scanning drive circuit, the processor, the scanning drive circuit, the data drive circuit and the display module are electrically connected, the scanning drive circuit is used for scanning a rising edge or a falling edge of the first clock indicator, of the second clock indicator and of the data indicator, and the data drive circuit is used for controlling pixels of the pixel group to be lit, according to the rising edge or the falling edge of the first clock indicator, of the second clock indicator and of the data indicator, wherein the controlled pixels of the pixel group to be lit having the second addresses matching the first clock indicator, the second clock indicator and the data indicator.

7. The living organism image monitoring system according to claim 5, wherein each of the plurality of CIGS modules comprises a MOS transistor and a CIGS diode, the CIGS diode is electrically connected with the MOS transistor, the MOS transistor is in a turned-on state when being charged, and the CIGS diode is used for being turned on to generate the current after detecting the near infrared light of the living organism.

8. The living organism image monitoring system according to claim 5, wherein the display module and the CIGS chip are integrally formed.

9. A living organism image monitoring method, being applicable to the living organism image monitoring system according to claim 1, the method comprising:
- a CIGS chip detecting a near infrared light of a living organism and generating a current after detecting the near infrared light of the living organism;
- a processor generating a first pulse according to the current;
- a display module displaying an image according to the first pulse;
- wherein the CIGS chip detecting the near infrared light of the living organism and generating the current after detecting the near infrared light of the living organism comprising:
  - each of a plurality of CIGS modules in the CIGS chip is provided with a first address, each CIGS module of the plurality of CIGS modules in the CIGS chip detecting the near infrared light of the living organism, one or more of the plurality of CIGS modules in the CIGS chip generating the current containing the first address after detecting the near infrared light of the living organism, wherein the plurality of CIGS modules in the CIGS chip are arranged according to a predetermined rule;
- wherein the processor generating the first pulse according to the current comprising:
  - the processor generating the first pulse after receiving the current that is transmitted by one or more of the plurality of CIGS modules and contains the first address, the processor acquiring a number of pixels of the display module and a number of CIGS modules included in the CIGS chip, calculating a ratio of the number of pixels of the display module to the number of CIGS modules included in the CIGS chip, and converting, according to the ratio, the first pulse to a second pulse, the number of pulses of the second pulse is equal to the number of pixels of the display module; and
- wherein the display module displaying the image according to the first pulse comprising:
  - the display module displaying an image according to the second pulse,
    - wherein the display module comprises a plurality of pixel groups, each pixel group of the plurality of pixel groups comprises one or more pixels, each CIGS module of the plurality of CIGS modules corresponds to one pixel group of the plurality of pixel groups, and the processor is used for controlling pixel groups to be lit, when any one of the plurality of CIGS modules detects infrared light, wherein the controlled pixel groups to be lit corresponding to the one of the plurality of CIGS modules,
    - wherein the plurality of pixel groups are arranged in a predetermined number of rows and a predetermined number of columns, and each pixel group of the plurality of pixel groups corresponds to a third address, the processor stores a correlation between third addresses and first addresses, and the processor is used for controlling the pixel group to be lit, when any one of the plurality of CIGS modules detects the infrared light, wherein the controlled pixel group to be lit having the third address corresponding to the first address of the one of the plurality of CIGS modules.

10. The living organism image monitoring method according to claim 9, wherein each of the CIGS modules of the plurality of CIGS modules comprises a MOS transistor and a CIGS diode, the CIGS diode is electrically connected with the MOS transistor;
- wherein the one or more CIGS modules of the plurality of CIGS modules generating the current containing the first address after detecting the near infrared light of the living organism comprises:
  - supplying power to the CIGS chip using a power supply, so that the MOS transistors of the plurality of CIGS modules in the CIGS chip are turned on; and
  - the CIGS diodes of the plurality of CIGS modules performing a near infrared light detection after the MOS transistors of the plurality of CIGS modules are turned on and being turned on after the near infrared light of the living organism is detected, and generating the current containing the first address.

11. The living organism image monitoring method according to claim 9, wherein the display module displaying the image according to the second pulse comprises:
- the processor controlling the pixel groups to be lit wherein the controlled pixel groups to be lit corresponding to CIGS modules that have detected the infrared light in the display module, wherein the display module comprises the plurality of pixel groups, each of the pixel groups of the plurality of pixel groups includes the one or more pixels, and each of the plurality of CIGS modules corresponds to one of the pixel groups of the plurality of pixel groups.

12. The living organism image monitoring method according to claim 11, wherein the processor controlling the pixel groups to be lit wherein the controlled pixel groups to be lit corresponding to the CIGS modules that have detected the infrared light in the display module comprises:
- the processor controlling the pixel groups to be lit, when any one of the plurality of CIGS modules detects the infrared light, the controlled pixel group to be lit having the third address corresponding to the first address of the CIGS module,
- wherein the processor stores the correlation between the third addresses and the first addresses.

* * * * *